US006638755B1

(12) United States Patent
Mizuochi et al.

(10) Patent No.: US 6,638,755 B1
(45) Date of Patent: Oct. 28, 2003

(54) SIMPLE CULTURE MEDIUM AND METHOD FOR PREPARATION THEREOF

(75) Inventors: Shingo Mizuochi, Yuuki (JP); Hidemasa Kodaka, Yuuki (JP); Hideaki Shibata, Yuuki (JP)

(73) Assignee: Nissui Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 09/926,551

(22) PCT Filed: May 16, 2000

(86) PCT No.: PCT/JP00/03128

§ 371 (c)(1), (2), (4) Date: Nov. 19, 2001

(87) PCT Pub. No.: WO00/71674

PCT Pub. Date: Nov. 30, 2000

(30) Foreign Application Priority Data

May 19, 1999 (JP) ............................................. 11-138811

(51) Int. Cl.[7] ............................. C12N 1/20; C12N 1/14; C12N 1/16; C12Q 1/04
(52) U.S. Cl. ................................ 435/253.6; 435/255.7; 435/256.8; 435/404; 435/431; 435/34
(58) Field of Search ........................... 435/253.6, 256.8, 435/404, 431, 255.7, 34

(56) References Cited

U.S. PATENT DOCUMENTS 5,494,823 A  *  2/1996  Takemoto et al.

FOREIGN PATENT DOCUMENTS

| | | | |
|---|---|---|---|
| JP | 57-94299 | | 6/1982 |
| JP | 60-49793 | | 3/1985 |
| JP | 6-181741 | | 7/1994 |
| JP | 8-286 | | 1/1996 |
| JP | 9-19282 | | 1/1997 |
| RU | 1791452 | * | 1/1993 |
| WO | WO 94/09151 | | 7/1994 |
| WO | WO 98/24883 | * | 6/1998 |
| WO | WO 98/31785 | | 7/1998 |

* cited by examiner

*Primary Examiner*—Sandra E. Saucier
*Assistant Examiner*—Vera Afremova
(74) *Attorney, Agent, or Firm*—Oblon, Spivak, McClelland, Maier & Neustadt P.C.

(57) ABSTRACT

A simple culture medium produced by impregnating a fibrous water-absorbent sheet with a suspension formed by suspending in an alcohol (a) an adhesive (0.01–0.4 wt. %) which is soluble in both water and alcohol, (b) a gelling agent which is soluble in water and insoluble in alcohol, and (c) a bacterial nutritive ingredient, the fibrous water-absorbent sheet having a mesh larger than the particle size of the gelling agent and being placed on a waterproof flat plate, and by drying the resultant sheet while suppressing rapid evaporation of the alcohol, to thereby cause the water-absorbent sheet to adhere onto the waterproof flat plate; and a method for producing the medium.

22 Claims, No Drawings

SIMPLE CULTURE MEDIUM AND METHOD FOR PREPARATION THEREOF

TECHNICAL FIELD

The present invention relates to a simple culture medium useful for, for example, detection, identification, and transportation of various microorganisms, and more particularly to a simple culture medium in which a test fluid inoculated thereto diffuses very rapidly and inoculation of a sample is possible even in an inclined state, an inverted state, or a gravity-free state.

BACKGROUND ART

Among conventional methods for culturing various microorganisms for detection and identification thereof, spread plate method, pour plate method, liquid medium method, etc. are generally employed. However, these methods require sterilization of culture medium, apparatus, etc. before culture of microorganisms, and inoculation of a test sample into the medium requires skilled operation such as spreading or pouring. Furthermore, when a conventional culture medium is sterilized after preparation of the medium or after hermetic packaging of the medium, maintaining the quality and performance of the medium during transportation and storage thereof is difficult; i.e., sterilization of the medium encounters difficulty.

Therefore, extensive studies have been performed on a simple culture medium which enables culture to be carried out easily, and a variety of culture devices and culture media have been proposed, including (1) a culture device in which an adhesive layer, a layer of a cold-water-soluble powdery gelling agent containing nutritive ingredients, and a cover sheet are successively laminated on the upper surface of a waterproof substrate (Japanese Patent Application Laid-Open (kokai) No. 57-502200); (2) a culture device in which a layer of a mixture of a cold-water-soluble gelling agent and a microorganism culture medium, and a fibrous water-absorbent sheet are successively laminated on the surface of a waterproof flat plate (Japanese Patent Application Laid-Open (kokai) No. 6-181741); and (3) a simple culture medium in which a medium composition containing an adhesive, a gelling agent, and a bacterial nutritive ingredient is carried with a fibrous water-absorbent sheet having a mesh larger than the particle size of the gelling agent (Japanese Patent Application Laid-Open (kokai) No. 9-19282).

However, the culture device in (1) above requires operations including careful application of an upper sheet and spreading of a test sample over a certain area by means of a spreader, and these operations must be carried out carefully on a flat plane such as a table; i.e., the culture device involves the problem of cumbersome inoculation operation. The culture device in (2) above involves problems in terms of preparation; i.e., insertion of the fibrous water-absorbent sheet after coating of the medium ingredients is troublesome, and the coating area of the medium ingredients must be greater than the area required for detection of microorganisms. In addition, since the fibrous water-absorbent sheet is not fixated, during inoculation, careful operation is required so as not to cause the sheet to move. The simple culture medium (3) involves problems in that the medium must be allowed to stand until a test fluid permeates and diffuses throughout the sheet, since the test fluid diffuses in the sheet slowly, and in that, even when the water-absorbent sheet is laminated and affixed onto a waterproof flat plate, the sheet is exfoliated from the plate very easily.

Accordingly, an object of the present invention is to provide a simple culture medium in which a test fluid inoculated thereto diffuses very rapidly, the medium containing a waterproof flat plate and a water-absorbent sheet reliably adhering onto the plate; enabling inoculation in an inclined state, an inverted state, or a gravity-free state, as well as in an even state; enabling detection and identification of microorganisms through a simple operation; and facilitating transportation, sterilization, etc. of the medium.

DISCLOSURE OF THE INVENTION

The present inventors have performed extensive studies in order to improve the aforementioned simple culture medium (3) (Japanese Patent Application Laid-Open (kokai) No. 9-19282), from the viewpoints of enhancement of the diffusion rate of a test fluid and reliable fixation of a sheet. As a result, the present inventors have found that, as compared with the case where an adhesive is incorporated in a large amount and a sheet impregnated with an alcohol suspension is dried in a usual manner, when the amount of an adhesive in an alcohol suspension containing a medium composition is reduced, a water-absorbent sheet is sufficiently impregnated with the suspension, and the resultant sheet is gradually dried, unexpectedly, the sheet can be caused to adhere onto a waterproof flat plate very strongly; and that there can be obtained a simple culture medium in which a test fluid diffuses at a very high rate; i.e., the test fluid instantaneously diffuses when inoculated into the medium. The present invention has been accomplished on the basis of these findings.

Accordingly, the present invention provides a simple culture medium produced by impregnating a fibrous water-absorbent sheet with a suspension formed by suspending in an alcohol (a) an adhesive (0.01–0.4 wt. %) which is soluble both in water and alcohol, (b) a gelling agent which is soluble in water and insoluble in alcohol, and (c) a bacterial nutritive ingredient, the fibrous water-absorbent sheet having a mesh larger than the particle size of the gelling agent and being placed on a waterproof flat plate, and by drying the resultant sheet while controlling rapid evaporation of the alcohol, to thereby cause the water-absorbent sheet to adhere onto the waterproof flat plate; and a method for producing the medium.

BEST MODE FOR CARRYING OUT THE INVENTION

An adhesive which serves as ingredient (a) of a medium composition must be soluble in water and alcohol. Examples of the adhesive include hydroxypropyl cellulose, polyvinyl pyrrolidone, and polyethylene oxide. Of these, hydroxypropyl cellulose is particularly preferred.

A gelling agent which serves as ingredient (b) must be soluble in water and insoluble in alcohol. Examples of the gelling agent include naturally occurring gelling agents such as xanthan gum, locust bean gum, guar gum, and carrageenan; and synthetic gelling substances such as hydroxyethyl cellulose. Of these, xanthan gum is particularly preferred. Such a gelling agent is preferably used in the form of powder having a mean particle size of 500 $\mu$m or less, particularly 0.5–50 $\mu$m.

A bacterial nutritive ingredient suitable for growth of a microorganism to be detected is chosen as ingredient (c). For example, when a variety of microorganisms are proliferated, typical nutritive medium ingredients are used, and when a specific microorganism is selectively proliferated, selected medium ingredients are used.

Preferably, a composition containing ingredients (a), (b), and (c) (hereinafter the composition will be referred to as "medium composition") further contains an appropriate color-developing agent for facilitating observation of colonies. Examples of the color-developing agent include dyes which color colonies, such as triphenyltetrazolium chloride, 3-(p-iodophenyl)-2-(p-nitrophenyl)-5-phenyl-2H-tetrazolium chloride, and 3-(4,5-dimethyl-2-thiazolyl)-2,5-diphenyl-2H-tetrazolium bromide; enzyme substrates such as 5-bromo-3-indolyl-β-D-galactoside; and pH indicators such as Bromothymol Blue and Neutral Red.

Examples of alcohols for suspending the medium composition include C1–C5 alcohols such as ethanol and 2-propanol.

The fibrous water-absorbent sheet in which the aforementioned medium composition is to be carried must allow an inoculated test fluid to diffuse readily by means of a capillary phenomenon for carrying thereon, and have a network structure capable of holding the gelling agent contained in the medium composition. To this end, the fibrous water-absorbent sheet must have a mesh larger than the particle size of the gelling agent, and a thickness larger than the particle size. For example, the fibrous water-absorbent sheet preferably has a mesh size of 15–100 mesh, particularly preferably 20–50 mesh, and preferably has a thickness of 10–1,000 μm, particularly preferably 50–600 μm.

Examples of the fibrous water-absorbent sheet include synthetic fiber unwoven cloth such as rayon unwoven cloth, and naturally occurring fiber unwoven cloth such as cotton unwoven cloth. The shape of the sheet is not particularly limited, and the sheet may assume a square shape, a rectangular shape, or a round shape. The size of the sheet is not particularly limited, but the longitudinal size of the sheet is preferably 1–15 cm when the sheet is to be used for simple detection of microorganisms.

A waterproof flat plate onto which the aforementioned fibrous water-absorbent sheet adheres may be formed from any waterproof material such as plastic or glass, but is preferably formed from transparent material so as to enable observation from the outside.

The simple culture medium of the present invention is produced as follows.

Firstly, medium ingredients (a) through (c) are added to alcohol, to thereby prepares an alcohol suspension. In this case, the concentration of ingredient (a) must be 0.01–0.4 wt. %, and is particularly preferably 0.01–0.15 wt. %. When the concentration of ingredient (a) of the alcohol suspension exceeds the above range, since movement of the medium ingredients of the suspension is limited by ingredient (a) of high concentration, the medium ingredients are dried and solidified merely in a sheet, resulting in unsatisfactory adhesion of the sheet onto a waterproof flat plate, as well as deterioration of water-absorbency of the sheet. The concentration of ingredient (b) of the alcohol suspension is preferably 0.1–20 wt. %, particularly preferably 2–6 wt. %; and the concentration of ingredient (c) of the alcohol suspension is preferably 0.5–20 wt. %, particularly preferably 1–5 wt. %.

Subsequently, a fibrous water-absorbent sheet placed on a waterproof flat plate is impregnated with the alcohol suspension by means of a technique such as pouring, spraying, or spreading. Preferably, the sheet is impregnated with the alcohol suspension containing the ingredients in the aforementioned concentrations in an amount of 0.5–2 mL on the basis of 1 cm$^3$ of the sheet. Thereafter, the alcohol is evaporated and removed through drying, to thereby cause the fibrous water-absorbent sheet carrying the medium ingredients to adhere onto the waterproof flat plate. Drying of the alcohol suspension must be carried out while rapid evaporation of the alcohol is suppressed. No particular limitation is imposed on the means for drying the alcohol suspension while rapid evaporation of the alcohol is suppressed. For example, drying is carried out in an atmosphere of high alcohol vapor pressure, or drying is carried out at low temperature.

As described above, when drying of the alcohol suspension is carried out gradually, the medium ingredients of the suspension are precipitated thoroughly in the course of drying, and after drying, the water-absorbent sheet strongly adheres onto the waterproof flat plate. Meanwhile, in the vicinity of the surface of the fibrous water-absorbent sheet, fiber filaments of the sheet are dried while the high water absorbency of the filaments is maintained, and thus, by means of the capillary phenomenon of cubic hollow portions formed by the filaments and the waterproof flat plate, the diffusion rate of a test fluid becomes high. As a result of the aforementioned phenomena, there can be produced the culture medium of the present invention, in which the diffusion rate of a test fluid is very high and the sheet is caused to adhere onto the waterproof flat plate very strongly. When the alcohol suspension is dried very rapidly, since the medium ingredients of the suspension are solidified while insufficiently precipitated, adhesion of the water-absorbent sheet onto the waterproof plate becomes unsatisfactory, and the diffusion rate of a test fluid is lowered.

The simple culture medium is preferably covered with a film or stored in a container, in order to prevent contamination and drying of the medium. Particularly preferred is the unit type such that the waterproof container, employed as a waterproof flat plate, is united by the successively laminated fibrous water-absorbent sheets with which the medium ingredients are carried.

The simple culture medium of the present invention produced as described above is preferably sterilized by means of, for example, ethylene oxide gas, γ-rays, or electron beams. Preferred sterilization methods include a method in which the simple culture medium is packed with a packaging material exhibiting both gas-barrier and light-shielding properties, such as an aluminum packaging material, and subsequently the packed medium is irradiated with, for example, γ-rays or electron beams. Particularly preferably, a drying agent is packed together with the simple culture medium during packaging. When the simple culture medium is sterilized through such a method, monitoring and controlling of all the medium production steps so as to maintain an antiseptic state is no longer necessary, and after sterilization, invasion of microorganisms into the medium and time-course change of the medium attributed to light and moisture can be prevented.

When detection of microorganisms is carried out by use of the simple culture medium of the present invention, a test fluid is inoculated into the surface of the medium. After inoculation, the test fluid diffuses readily in the medium by means of the capillary phenomenon of cubic hollow portions formed between meshes, followed by occurrence of swelling and gelation; microorganisms contained in the test fluid are trapped in the resultant gel; free movement of the microorganisms is suppressed; and colonies are formed through culture. Therefore, through observation of the surface of the medium, the thus-formed colonies can be easily observed. When a sample is quantitatively inoculated into the simple culture medium, the number of bacteria contained in the sample can be easily calculated by counting colonies formed after culture of the sample.

Inoculation of a bacterial fluid into the simple culture medium is usually carried out through a method in which a certain amount of the fluid is inoculated into the medium by use of, for example, a pipette; but may be carried out through a method in which the medium is stamped onto a living organism containing a large amount of water, or a method in which the medium is immersed in a sample. After a test fluid is inoculated into the simple culture medium, culture in the medium may be carried out while the medium is allowed to stand or while the medium is transported.

EXAMPLES

The present invention will next be described in more detail by way of Examples, which should not be construed as limiting the invention thereto.

Example 1
(1) Preparation of Culture Medium

Peptone (1.0 g), yeast extract (0.5 g), glucose (0.2 g), xanthane gum (3 g), and tetrazolium chloride (0.002 g) were added to an ethanol solution (100 mL) containing 0.01–1 wt. % hydroxypropyl cellulose (HPC), to thereby prepare a suspension. The thus-prepared ethanol suspension (1 mL) was poured into two containers (50 φmm), each containing a fibrous water-absorbent sheet (50 φmm), and the two containers were stacked one on the other and gradually dried in a closed space overnight. Thereafter, each of the containers was capped, to thereby produce the simple culture medium of the present invention. The present simple culture medium and a drying agent were hermetically packed with an aluminum packaging material, and then sterilized through γ-ray irradiation at a surface dose of 10–20 kGy.

Since the water-absorbent sheet was reliably affixed onto the container in the simple culture medium, inoculation into the medium could be carried out in an inclined state or an inverted state.

(2) Diffusibility test

Purified water (1 mL) was added dropwise to the center portion of the water-absorbent sheet of the present simple culture medium, and the time until the water diffused throughout the container was measured. The results are shown in Table 1.

with an aluminum packaging material, and then sterilized through electron-beam irradiation or γ-ray irradiation at a surface dose of 10–20 kGy. Thereafter, the below-described test was carried out.

*Escherichia coli* was cultured in Tryptosoya broth (product of Nissui Pharmaceutical Co., Ltd.) at 35° C. for 24 hours, and the *E. coli* culture was diluted stepwise (to 1/10 in each step). An aliquot (1 mL) from each dilution was inoculated into culture media of the present invention (sterilized through electron-beam irradiation or through γ-ray irradiation) and into a standard method agar culture medium (product of Nissui Pharmaceutical Co., Ltd.), and cultured at 35° C. for 48 hours. Thereafter, the number of colonies was counted.

From the results of tests which were carried out five times, an average colony count in each of the culture media was calculated: $2.6 \times 10^8$ cfu/mL in the culture medium of the present invention sterilized through electron-beam irradiation, $2.7 \times 10^8$ cfu/mL in the culture medium of the present invention sterilized through γ-ray irradiation, and $2.7 \times 10^8$ cfu/mL in the standard method agar culture medium.

The results show that the colony count is substantially the same in all the culture media, and that there is no difference between the culture media in bacterial growth performance.

Example 3

Peptone (1.0 g), yeast extract (0.5 g), glucose (0.2 g), xanthan gum (3 g), and tetrazolium chloride (0.002 g) were added to an ethanol solution (100 mL) containing 0.1 wt. % hydroxypropyl cellulose (HPC), to thereby prepare a suspension. The thus-prepared ethanol suspension (1 mL) was poured into two containers (50 φmm), each containing a fibrous water-absorbent sheet (50 φmm), the two containers were stacked one on the other, and gradually dried in a closed space while alcohol gas was displaced by air. Thereafter, each of the containers was capped, to thereby produce the culture medium of the present invention. The present simple culture medium and a drying agent were hermetically packed with an aluminum packaging material, and then sterilized through γ-ray irradiation at a surface dose of 10–20 kGy.

TABLE 1

(Unit: second)

| Position of container During drying | Concentration of hydroxypropyl cellulose (wt. %) | | | | | | | | | |
|---|---|---|---|---|---|---|---|---|---|---|
| | 0.01 | 0.05 | 0.1 | 0.15 | 0.2 | 0.25 | 0.3 | 0.4 | 0.5 | 1.0 |
| Upper | 2.12 | 2.98 | 4.37 | 5.68 | 9.35 | 11.14 | 13.12 | 16.99 | 65.97 | 43.29 |
| Lower | 3.21 | 4.89 | 7.34 | 5.65 | 11.20 | 10.41 | 16.48 | 16.30 | 42.26 | 44.72 |

As is apparent from Table 1, when the HPC concentration is 0.4 wt. % or less, the medium exhibits good diffusibility, and particularly when the HPC concentration is 0.15 wt. % or less, the medium exhibits excellent diffusibility: i.e., the purified water diffuses very rapidly (within 10 seconds) throughout the medium.

Example 2

A culture medium produced in a manner similar to that of Example 1 and a drying agent were hermetically packed Since the water-absorbent sheet was reliably affixed onto the container in the culture medium, inoculation into the medium could be carried out in an inclined state or an inverted state.

Purified water (1 mL) was added dropwise to the center portion of the water-absorbent sheet of the present culture medium, and the time until the water diffused throughout the container was measured. The time was 5.53 seconds; i.e., the medium exhibited good diffusibility.

Industrial Applicability

The simple culture medium of the present invention provides very rapid (instantaneous) diffusion of a test fluid inoculated into the medium. In addition, inoculation into the medium can be carried out regardless of the posture—inclined or inverted—of the medium, or even under gravity-free. Therefore, through use of the medium, a microbial test can be carried out rapidly in a simple manner in any place; for example, indoors, outdoors, or in space.

What is claimed is:

1. A simple culture medium, comprising (a) an adhesive, (b) a gelling agent, (c) a bacterial nutritive ingredient, a fibrous water-absorbent sheet, and a waterproof flat plate, produced by a process comprising:

preparing an alcohol suspension by suspending in an alcohol (a) an adhesive, which is soluble in both water and alcohol, and is a hydroxypropyl cellulose, at a final concentration of 0.01 to 0.4% w/v (b) a gelling agent, which is soluble in water and insoluble in alcohol, and (c) a bacterial nutritive ingredient;

impregnating a fibrous water-absorbent sheet with the alcohol suspension, wherein the fibrous water-absorbent sheet has a mesh larger than the particle size of the gelling agent and being placed on a waterproof flat plate; and drying the resultant sheet while suppressing rapid evaporation of alcohol, to thereby cause the water-absorbent sheet to adhere onto the waterproof flat plate.

2. The simple culture medium according to claim 1, wherein the ingredient (b) is selected from the group consisting of xanthan gum, locust bean gum, guar gum, carrageenan, and hydroxyethyl cellulose.

3. The simple culture medium according to claim 1, wherein the ingredient (b) is a powder having a mean particle size of 0.5–50 $\mu$m.

4. The simple culture medium according to claim 1, wherein the alcohol suspension further comprises a color-developing agent.

5. The simple culture medium according to claim 1, wherein the alcohol is a $C_1$–$C_5$ alcohol.

6. The simple culture medium according to claim 1, wherein the fibrous water-absorbent sheet has a mesh size of 15–100 mesh, and a thickness of 10–1,000 $\mu$m.

7. A method for producing a simple culture medium, comprising preparing an alcohol suspension by suspending in an alcohol (a) an adhesive, which is soluble in both water and alcohol, and is a hydroxypropyl cellulose, at a final concentration of 0.01 to 0.4% w/v (b) a gelling agent, which is soluble in water and insoluble in alcohol, and (c) a bacterial nutritive ingredient;

impregnating a fibrous water-absorbent sheet with the alcohol suspension, wherein the fibrous water-absorbent sheet has a mesh larger than the particle size of the gelling agent and wherein the water-absorbent sheet is placed on a waterproof flat plate; and drying the resultant sheet while suppressing rapid evaporation of alcohol, to thereby cause the water-absorbent sheet to adhere onto the waterproof flat plate.

8. The method according to claim 7, wherein ingredient (b) is selected from the group consisting of xanthan gum, locust bean gum, guar gum, carrageenan, and hydroxyethyl cellulose.

9. The method according to claim 7, wherein ingredient (b) is a powder having a mean particle size of 0.5–50 $\mu$m.

10. The method according to claim 7, wherein the alcohol suspension further comprises a color-developing agent.

11. The method according to claim 7, wherein the alcohol is a $C_1$–$C_5$ alcohol.

12. The method according to claim 7, wherein the fibrous water-absorbent sheet has a mesh size of 15–100 mesh, and a thickness of 10–1,000 $\mu$m.

13. The simple culture medium according to claim 4, wherein the color-developing agent is selected from the group consisting of triphenyltetrazolium chloride, 3-(p-iodophenyl)-2-(p-nitrophenyl)-5-phenyl-2H-tetrazolium chloride, 3-(4,5-dimethyl-2-thiazolyl)-2,5-diphenyl-2H-tetrazolium bromide, 5-bromo-3-indolyl-β-D-galactoside, bromothymol blue, and neutral red.

14. The simple culture medium according to claim 5, wherein the $C_1$–$C_5$ alcohol is ethanol or 2-propanol.

15. The simple culture medium according to claim 1, wherein the fibrous water-absorbent sheet is a synthetic fiber unwoven cloth or a naturally occurring fiber unwoven cloth.

16. The simple culture medium according to claim 1, wherein the fibrous water-absorbent sheet is a rayon unwoven cloth or a cotton unwoven cloth.

17. The simple culture medium according to claim 1, wherein the waterproof flat plate comprises plastic or glass.

18. The method according to claim 10, wherein the color-developing agent is selected from the group consisting of triphenyltetrazolium chloride, 3-(p-iodophenyl)-2-(p-nitrophenyl)-5-phenyl-2H-tetrazolium chloride, 3-(4,5-dimethyl-2-thiazolyl)-2,5-diphenyl-2H-tetrazolium bromide, 5-bromo-3-indolyl-β-D-galactoside, bromothymol blue, and neutral red.

19. The method according to claim 11, wherein the $C_1$–$C_5$ alcohol is ethanol or 2-propanol.

20. The method according to claim 7, wherein the fibrous water-absorbent sheet is a synthetic fiber unwoven cloth or a naturally occurring fiber unwoven cloth.

21. The method according to claim 7, wherein the fibrous water-absorbent sheet is a rayon unwoven cloth or a cotton unwoven cloth.

22. The method according to claim 7, wherein the waterproof flat plate comprises plastic or glass.

* * * * *